United States Patent [19]

Poler

[11] 4,315,336
[45] Feb. 16, 1982

[54] INTRAOCULAR LENS

[76] Inventor: Stanley Poler, 78 E. Second St., New York, N.Y. 10003

[21] Appl. No.: 113,967

[22] Filed: Jan. 21, 1980

[51] Int. Cl.³ ............................ A61F 1/16; A61F 1/24
[52] U.S. Cl. ........................................ 3/13; 156/182; 156/196
[58] Field of Search ............................................ 3/13, 1

[56] References Cited

U.S. PATENT DOCUMENTS

| | | | |
|---|---|---|---|
| 2,834,023 | 5/1958 | Lieb | 3/13 X |
| 4,087,866 | 5/1978 | Choyce et al. | 3/13 |
| 4,134,161 | 1/1979 | Bayers | 3/13 |
| 4,206,518 | 6/1980 | Jardon et al. | 3/13 |

FOREIGN PATENT DOCUMENTS

| | | | |
|---|---|---|---|
| 959314 | 3/1957 | Fed. Rep. of Germany | 3/13 |
| 810232 | 3/1959 | United Kingdom | 3/13 |

OTHER PUBLICATIONS

"A Lens for all Seasons", (Book), by Jerald L. Tennant, Aug. 1976, pp. 13-21.
"A Weightless Iseikonic Intraocular Lens", by Richard D. Binkhorst, American Journal of Ophthalmology, vol. 58, No. 1, Jul. 1964, pp. 73-78.

Primary Examiner—Ronald L. Frinks
Attorney, Agent, or Firm—Hopgood, Calimafde, Kalil, Blaustein & Judlowe

[57] ABSTRACT

The invention contemplates intraocular lens configurations wherein a haptic element is secured to an optically-finished glass lens element and is particularly adapted for implantation in the anterior chamber of an eye and for stabilized central positioning solely through plural positioning contacts with the inner confines of the anterior chamber, at the angle of adjacency to the iris, commonly referred to as the anterior-chamber angle. All-glass configurations are described, wherein the haptic element is glass and is fused or otherwise secured to the lens element.

17 Claims, 11 Drawing Figures

INTRAOCULAR LENS

BACKGROUND OF THE INVENTION

The invention relates to intraocular lenses particularly suited for anterior-chamber implantation in the human eye, relying solely upon anterior-chamber features for stabilized optically correct location.

Prior lenses of the character indicated are exemplified by those disclosed in Choyce, et al., U.S. Pat. No. 4,087,866, in Bayers U.S. Pat. No. 4,134,161, and in the technical paper entitled "Surgical Complications of Choyce-Type Implants", by R. H. Keates, et al., presented at the 1978 Annual Meeting of the American Academy of Ophthalmology, Symposium on Intraocular Lenses. As far as I am aware, all such prior lenses have been of plastic construction, and they are tissue-reactive, in the sense that tissue growth is not retarded and can become a clouding factor to degrade optical performance of the implant. With present lenses, sterilization must be accomplished using a caustic solution or ethylene oxide gas*. Such lenses are injection-molded products and therefore cannot be classed with the quality of an optically finished glass lens. But glass lenses as implants have been generally shunned, primarily because of the high specific gravity of glass, as compared to that of plastic; see Binkhorst, et al., "A Weightless Iseikonic Intraocular Lens", American Journal of Ophthalmology, Vol. 58, No. 1, July 1964, pp. 73 to 78. And, in particular, it is noted that although Choyce, et al. U.S. Pat. No. 4,087,866 mentions glass as a possible lens material, the disclosure is silent on any suggestion of optically finished glass for the purpose.

*A glass anterior chamber lens would allow for autoclaving.

BRIEF SUMMARY OF THE INVENTION

It is an object of the invention to provide an improved intraocular lens and method of making the same.

It is a specific object to achieve the above object with structure which is tolerably self-stabilizing solely within the anterior chamber of the eye.

It is another specific object to meet such objects using a single optically finished glass lens element, thus assuring high optical quality.

Another specific object is to achieve the foregoing objects with structure which is inherently not tissue-reactive and which is inherently much less likely to encounter a clouding tissue growth than is the case for prior lens constructions.

Another object is to provide for autoclavable devices, of the character indicated.

Still another specific object is to produce an all-glass intraocular lens and haptic, with a central optically finished refractive region.

A general object is to meet the above objects with structure which can be reliably manufactured in production quantities, at relatively low cost for the inherent high optical quality involved.

The foregoing and other objects and features on the invention are achieved in configurations wherein the haptic is of thin glass sheet, of uniform thickness, and has external-edge contouring and other formations suited for foot-stabilizing contact at the anterior-chamber angle of the eye. In one general form, the central region of the haptic is flat, and the plane-surface side of a plano-convex glass lens, optically finished to desired power, is secured to the flat of the haptic, as by fusing, cementing or the like. In another general form, the optically finished glass lens need not be plano-convex, but it is of circular outer-edge contour, being inserted in and secured to the inner edge of a suitably sized opening in the haptic.

DETAILED DESCRIPTION

The invention will be described for various illustrative forms, in conjunction with the accompanying drawings, in which.

Figure 1:
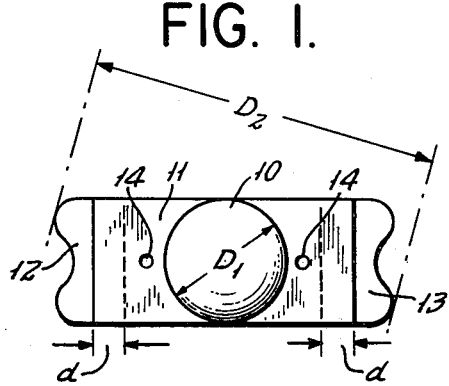
FIG. 1 is a plan view of an anterior-chamber lens and haptic of the invention.
Figure 2:
FIG. 2 is a side view of the lens and haptic of FIG. 1.

In the configuration of FIGS. 1 and 2, an intraocular assembly comprises a circular optically finished plano-convex lens 10 of diameter $D_1$ secured centrally to an elongate haptic base 11 of thin flat glass sheet, the plane side of lens 10 being in intimate continuous adjacency to one of the surfaces of the sheet 11. The sheet 11 is of width $D_1$ and extends longitudinally beyond diametrically opposite regions of the lens, but its maximum longitudinal extent is short of the mounting diameter $D_2$ dictated by the inner confines of the anterior chamber of an eye, at the so-called "angle", namely the groove or space between the scleral ridge and the iris. The diametral span $D_2$ varies, generally 12 to 14 mm, depending on size of the eye, and it is important for avoidance of trauma that the span $D_2$ of the haptic be selected correctly, within the indicated range. In the form shown, the span $D_2$ is provided to appropriate length by means of foot elements 12-13, also of glass sheet, and secured to one of the surfaces of the base 11, at symmetrical longitudinal-overlap regions d.

The indicated securing of lens 10 to haptic 11 is preferably achieved by fusing the two elements, using a suitable frit. Alternatively, an optical cement inert to body fluids may be employed, selected from commercially available varieties, including sodium silicate, balsam compounds, benign epoxies, and UV-cured optical cements. What has been said as to securing lens 10 to the haptic base 11 applies also to the securing of feet 12-13 to base 11. In fact, in a preferred technique, a lens 10 of desired power is correctly located with respect to base 11 by jig means (not shown), which also includes adjustable means for selecting the span $D_2$ at which the foot elements are to be positioned; then, in one fusing operation, all the parts 10-11-12-13 are correctly secured to each other.

The described structure will be seen not only to achieve correctly centered lens mounting to a haptic of preselected span $D_2$, but also to provide an axial offset, to the extent of the thickness $t_1$ of elements 12-13, for the foot elements with respect to the base 11. For an all-glass structure of light weight and adequate strength, the foot thickness $t_1$ is typically about a quarter millimeter, as is also the thickness $t_2$ of the haptic base 11. And the lens 10 is of 5 mm diameter ($D_1$) and of maximum thickness, approximating 0.4 mm. The indicated preference for fusing the parts not only assures bonding of a structure which is exclusively glass, but it (fusing) so heats the parts as to round (smooth out) all edges. The completed structure thus represents best chances for successful implantation, and for utmost resistance to post-operative tissue growth, as well as secured sterilization by autoclaving.

The outer contouring of foot elements 12–13 may be as the individual suregon may prefer. The contour may thus for example be generally a circular arc about the optical axis of the lens, or, as shown, it may in each case comprise a pair of spaced foot projections or lobes; it is noted that when using two lobes per foot, as shown in FIG. 1, the critical overall length dimension $D_2$ is the maximum diagonal extent, between diagonally opposite lobes. To complete the description of FIGS. 1 and 2, small apertures 14 in base 11, on opposite sides of lens 10, and inwardly offset from any possible foot-element overlap d, enable simple manipulative control of the assembly, as by tweezers. These holes may also be used by a physician to manipulate the lens during insertion.

Figure 2A:
FIGS. 2A and 3 are views similar to that of FIG. 2, to show modifications.

The form of FIG. 2A in all respects resembles that of FIG. 2 except that the lens 10 in FIG. 2A is mounted on the posterior side of base 11, rather than on the anterior side as in FIG. 2. This option provides latitude for professional selection of optical performance suited to the needs of particular patients and the surgeon's preference; mounting lenses posteriorly also allows for greater clearance between the cornea and lens. And, since the structure is all-glass, no adverse reaction ensues from the fact that in the region of iris dilation or contraction, a flat surface of base 11 may contact the iris (FIG. 2) or the convex surface of lens 10 may contact the iris (FIG. 2A), it being noted that in both bases the minimum dimension $D_1$ of the implant exceeds maximum dilation of an iris.

Figure 3:
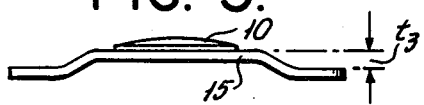

In the arrangement of FIG. 3, the lens 10 is as previously described and is secured to the flat central region of an elongate glass-sheet haptic 15, the ends of which have been axially offset to a preselected extent $t_3$, as by slumping to conformance with a slumping mold or form (not shown), which may be accomplished at the time of fusing lens 10 to the haptic.

It will be understood that the peripheral contour of haptic 15 may match that of the fused parts 11-12-13 in FIG. 1; alternatively, foot elements 12–13 may be applied to the slumped ends of a shortened base 15, to achieve a prescribed overall span $D_2$. It will further be understood that lens 10 may optionally be mounted to haptic 15 on the side of offset $t_3$ or on the opposite side, as shown.

Figure 4:
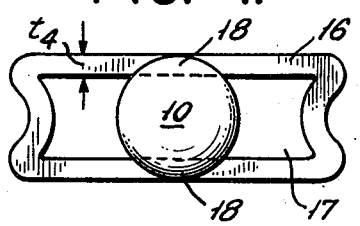
FIGS. 4, 5, 6 and 7 are views similar to that of FIG. 1, to show modifications.

The embodiment of FIG. 4 represents substantial economy of haptic weight in a structure which in its side elevation may generally resemble that of FIG. 3. In particular, in FIG. 4 the haptic 16 derives from glass sheet of uniform thickness, which for simplicity is shown with the same external profile as appears in FIG. 1. Weight economy results from provision of a large centrally open area 17, meaning that the haptic 16 is a peripherally continuous ribbon of slumped glass sheet. The ribbon width $t_4$ may suitably be 1 to 2 mm, with bonded connection to the plane surface of lens 10 at diametrically opposed chordal regions 18 of overlap. The actual definition of haptic 16 from flat sheet glass, may be pursuant to photo-etch techniques similar to those discussed in my U.S. Pat. No. 4,080,709.

Figure 5:
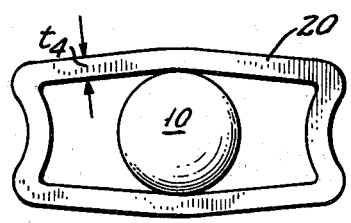

In the form of FIG. 5, the haptic 20 is again a continuous ribbon frame of width $t_4$, preferably of glass slumped to the elevational profile shown at 15 in FIG. 3. In FIG. 5, however, the fused or cemented attachment of lens 10 to haptic 20 is at diametrically opposite tangential-edge contacts. The mounting of the lens 10 thus does not dictate that lens 10 be plano-convex; it may therefore be more complex, for example, a meniscus (concavo-convex) lens. The form of FIG. 5 thus presents the surgeon with further latitude as to lens prescription for the patient.

Figure 6:
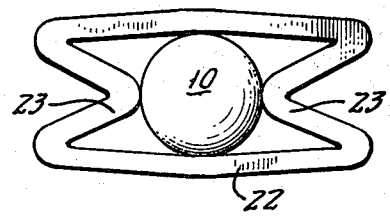

The form of FIG. 6 resembles that of FIG. 5 except that between the individual foot lobes or projections at each longitudinal end of the ribbon haptic 22, the ribbon frame converges radially inward at 23, to tangential contact with diametrically opposed regions of the circular edge of lens 10, these contact regions being 90 degrees offset from the similar lens contacts of the longitudinal sides of the haptic. All four contacts are secured, as by fusing or cementing, with resultant more positive four-point support for the lens 10. Again, a meniscus lens may be used at 10, if desired.

Figure 7:
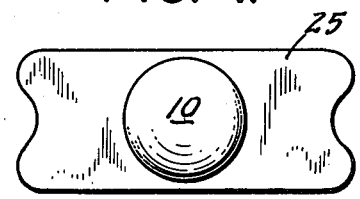
Figure 8:
FIGS. 8 and 9 are longitudinal sectional views, taken of FIG. 7, to show alternative forms.
Figure 9:
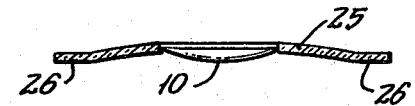

The embodiment of FIG. 7 illustrates the invention in the circumstance that the opening within haptic 25, again a thin sheet of uniformly thick glass, is circular and substantially conforms to the external edge contour of the lens element 10, inserted in the opening. In FIG. 8, the haptic 25 is flat at its central region of lens support, being slumped to produce axially offset foot elements, as suggested by phantom outlines 26. In FIG. 9, the haptic 25 is arcuately bowed to produce the desired offset, with outer foot formations extending in a single plane at the offset location. In the FIG. 8 or in the FIG. 9 situation, the haptic may be slumped to desired offsetting profile prior to or in the course of fused assembly of the lens element 10 thereto.

Figure 10:
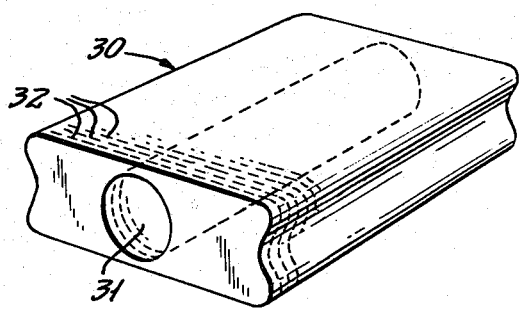
FIG. 10 is a view in perspective to illustrate part of a method of making many of the haptics in the foregoing embodiments.

FIG. 10 illustrates a currently preferred technique of producing glass haptics of the invention, to the uniformly thin proportions indicated. An elongate prismatic block 30 of glass is selected and shaped, as by grinding, to a desired uniform section, the section visible directly in FIG. 10 being recognizably the haptic planiform shown at 25 in FIG. 7. The central circular lens-mounting opening is defined in the uniform section, by making a cylindrical bore 31 in the glass block 30. When shaped to desired internal and external profiles, individual haptics are created by slicing, as with a circular diamond saw, along cut alignments suggested in phantom at 32. The subsequent fusing and/or slumping processes, such as flaming, on such sliced haptics sufficiently smooth all surfaces and edges of the slices as to require no further finishing steps, even for the situation, as in FIGS. 1 to 4 wherein the plane surface of the lens 10 is secured directly and intimately to one of the flat surfaces of the haptic.

The various described embodiments of the invention will be seen to have achieved all stated objects. In particular, at least to my knowledge, the invention provides for the first time the opportunity to create a lightweight intraocular lens for anterior-chamber mounting that is all-glass and which also provides precision-ground optically finished lens elements. The all-glass features are of particular importance in rendering the resulting product most non-reactive to body fluids and tissue and securely sterilized by autoclaving, and the ophthalmologist has much greater latitude than heretofore, in practically obtaining (at 10) the precise lens prescription which is deemed best for the patient. Stated in other words, an inventory of lens elements 10, of various optical power and other specification, may be readily drawn upon to complete intraocular lens assemblies of the invention, when and as needed. And preformed haptics, ready to receive lenses as selected from such inventory, may themselves be preformed to desired offsets $t_3$ and to various spans $D_2$, in separate inventory, all then being in readiness for swift selection and completion by assembly to a prescribed lens 10, as may be best suited for the individual patient.

While the invention has been described in detail for the forms shown, it will be understood that modifications may be made without departure from the claimed scope of the invention. For example, a high-temperature material other than glass, such as an autoclavable plastic or ceramic may be used for the described haptic structure. Also, for example, in embodiments wherein the lens element is inserted in a haptic opening of matching peripheral contour, the permanent fixed retention of the lens-to-haptic assembly may be achieved by differential-shrinking, as by first heat-expanding the haptic and/or chilling the lens element before allowing the assembled parts to return to ambient temperature.

Still further, although the lens element 10 has been described as either plano-convex or concavo-convex, and as being optically-finished, i.e., precision-ground, it will be understood that such lens element may be prescription-ground, as with a cylindrical or eccentric component of curvature to provide astigmatism correction, in which case the transverse axis of such correction will have been established. This being the case, the lens element 10 with such corrective properties may be assembled with predetermined rotational orientation with respect to a known ultimate axis of haptic implantation in an eye. For example, in FIG. 1, the manipulation apertures 14 visually certify the alignment of the longitudinal axis of the haptic, and if the surgeon elects to implant with this alignment vertical (or horizontal), then the correction axis of lens element 10 will have been so angularly oriented to the haptic axis as to establish the desired axis of correction for the patient. It is understood that, based on pre-operative measurement of a patient's astigmatism (e.g., by analysis of his last pair of spectacles), an experienced ophthalmological surgeon can closely predict the degree and orientation of astigmatism-correction needed post-operatively, thereby enabling the predicted correction to be "built into" the intraocular lens.

What is claimed is:

1. As an article of manufacture, an optically finished plano-convex glass intraocular lens element, and a mounting adapter for said lens element, said adapter comprising a single piece of plane-parallel glass, the flat surface of said lens element being in secured intimate adjacency to one of the surfaces of said adapter piece, said adapter piece extending radially outward of said lens element at locations angularly spaced about the optical axis of said lens element.

2. The article of claim 1, in which said adjacent surfaces are fused.

3. The article of claim 1, in which said adjacent surfaces are cemented.

4. The article of claim 1, in which at said radially outwardly extending locations said adapter comprises stabilizing foot formations which are axially offset to the same extent and in one direction away from the plane of said adjacent surfaces.

5. The article of claim 4, in which the convex surface of said lens element projects axially in the direction of said offset.

6. The article of claim 4, in which the convex surface of said lens element projects axially in the direction opposite to said offset.

7. As an article of manufacture, an optically finished plano-convex glass intraocular lens element, and a mounting adapter for said lens element, said adapter comprising a single piece of plane-parallel glass, the flat surface of said lens element being in secured intimate adjacency to one of the surfaces of said adapter piece, said adapter piece extending radially outward of said lens element at locations angularly spaced about the optical axis of said lens element, said single piece of plane-parallel glass being flat and projecting in diametrically opposite directions beyond said lens element, the radial extent of the projecting ends of said single piece of plane-parallel glass with respect to the optical axis of said lens element being less than the inside radius of the scleral spur of a human eye, first and second flat glass foot elements secured to one of the flat surfaces of said projecting ends and in like radially overlapping intimate adjacency thereto, said foot elements extending by equal offsets radially beyond the projecting ends of said single piece of plane-parallel glass, whereby depending upon the secured overlap of said foot elements with said single piece of plane-parallel glass, the outer limits of said foot elements may be of such overall effective span as to provide optimal mounted accommodation through scleral-ridge retention in the anterior chamber of an eye, with the foot elements providing forwardly offset mounting of the lens element with respect to an iris.

8. As an article of manufacture, an optically finished plano-convex glass intraocular lens element, and a mounting adapter for said lens element, said adapter comprising a single piece of plane-parallel glass, the flat surface of said lens element being in secured intimate adjacency to one of the surfaces of said adapter piece, said adapter piece extending radially outward of said lens element at locations angularly spaced about the optical axis of said lens element, said piece of plane-parallel glass being characterized by a peripherally continuous external contour in the form of a relatively narrow ribbon enclosing an open space having a minimum span which is less than the diameter of said lens element, diametrically opposite regions of said lens element being secured to said piece of plane-parallel glass at like chordal registrations with said ribbon at the minimum-span region thereof.

9. As an article of manufacture, an optically finished plano-convex glass intraocular lens element, and a mounting adapter for said lens element, said adapter comprising a single piece of plane-parallel autoclavable material, the flat surface of said lens element being in secured intimate adjacency to one of the surfaces of said adapter piece, said adapter piece extending radially outward of said lens element at locations angularly spaced about the optical axis of said lens element, said single piece of plane-parallel autoclavable material being flat and projecting in diametrically opposite directions beyond said lens element, the radial extent of the projecting ends of said single piece of plane-parallel autoclavable material with respect to the optical axis of said lens element being less than the inside radius of the scleral spur of a human eye, first and second flat foot elements of autoclavable material secured to one of the flat surfaces of said projecting ends and in like radially overlapping intimate adjacency thereto, said foot elements extending by equal offsets radially beyond the projecting ends of said single piece of plane-parallel autoclavable material, whereby depending upon the secured overlap of said foot elements with said single piece of plane-parallel autoclavable material the outer limits of said foot elements may be of such overall effective span as to provide optimal mounted accommodation through scleral-ridge retention in the anterior chamber of an eye, with the foot elements providing forwardly offset mounting of the lens element with respect to an iris.

10. As an article of manufacture, an optically finished plano-convex glass intraocular lens element, and a mounting adapter for said lens element, said adapter comprising a single piece of plane-parallel autoclavable material, the flat surface of said lens element being in secured intimate adjacency to one of the surfaces of said adapter piece, said adapter piece extending radially outward of said lens element at locations angularly spaced about the optical axis of said lens element, said adapter being characterized by at least one transverse-axis reference indicium, and said lens element being optically finished with a correction for astigmatism, the correction axis being at a predetermined angular orientation with respect to said indicium.

11. As an article of manufacture, an optically finished glass intraocular lens element, and a mounting adapter for said lens element, said adapter comprising an elongate sheet of autoclavable material of uniform thickness and having a central opening having an inner-edge contour for circumferentially continuous bodily reception of the outer-edge contour of said lens element, said lens element being secured to said sheet via said contours, said sheet having an outer-edge contour adapted for foot-stabilized positioning in the anterior chamber of an eye, said adapter being characterized by at least one transverse-axis reference indicium, and said lens element being optically finished with a correction for astigmatism, the correction axis being at a predetermined angular orientation with respect to said indicium.

12. As an article of manufacture, an optically finished glass intraocular lens element, and a mounting adapter for said lens element, said adapter comprising a single elongate sheet of plane-parallel glass characterized by a peripherally continuous external contour in the form of a relatively narrow ribbon enclosing an open space of larger area than the area of said lens element, said sheet having stabilizing-foot contour regions at the respective longitudinal ends of said sheet, said ribbon in the region between said longitudinal ends defining generally chordal spans having central diametrically opposite secured engagement with said lens element.

13. The article of claim 12, in which said stabilizing-foot contour regions are two in number at each of the longitudinal ends of said sheet, the contour of said ribbon undulating radially inwardly between each pair of stabilizing-foot contour regions.

14. The article of claim 13, in which said inward undulations extend to secured contact with diametrically opposed outer-edge regions of said lens element.

15. The article of claim 1 or claim 12, in which said lens element is of circular outer-edge profile, at a maximum diameter of substantially 5 millimeters.

16. The article of claim 1 or claim 12, in which the mounting-adapter glass is of approximately 0.25 millimeter thickness.

17. As an article of manufacture, an optically finished plano-convex glass intraocular lens element, and a mounting adapter for said lens element, said adapter comprising a single piece of plane-parallel autoclavable material, the flat surface of said lens element being in secured intimate adjacency to one of the surfaces of said adapter piece, said adapter piece extending radially outward of said lens element at locations angularly spaced about the optical axis of said lens element, said piece of plane-parallel autoclavable material being characterized by a peripherally continuous external contour in the form of a relatively narrow ribbon enclosing an open space having a minimum span which is less than the diameter of said lens element, diametrically opposite regions of said lens element being secured to said piece of plane-parallel glass at like chordal registrations with said ribbon at the minimum-span region thereof.

* * * * *